(12) United States Patent
Kuh et al.

(10) Patent No.: US 10,983,031 B2
(45) Date of Patent: Apr. 20, 2021

(54) METHOD FOR PRODUCING SAMPLE SLICE (71) Applicants: THE CATHOLIC UNIVERSITY OF KOREA INDUSTRY-ACADEMIC COOPERATION FOUNDATION, Seoul (KR); MBD KOREA, CO., LTD., Gyeonggi-do (KR)

(72) Inventors: Hyo Jeong Kuh, Seoul (KR); Ji Hoon Kang, Gwangju (KR); Dong Wo Lee, Gyeonggi-do (KR)

(73) Assignees: THE CATHOLIC UNIVERSITY OF KOREA INDUSTRY-ACADEMIC COOPERATION FOUNDTION, Seoul (KR); MBD KOREA, CO., LTD., Gyeonggi-Do (KR)

( * ) Notice: Subject to any disclaimer, the term of this patent is extended or adjusted under 35 U.S.C. 154(b) by 0 days.

(21) Appl. No.: 16/653,662

(22) Filed: Oct. 15, 2019

(65) Prior Publication Data
US 2020/0041386 A1 Feb. 6, 2020

Related U.S. Application Data (62) Division of application No. 15/347,767, filed on Nov. 9, 2016, now abandoned.

(30) Foreign Application Priority Data

Mar. 11, 2016 (KR) .................. 10-2016-0029321
Oct. 26, 2016 (KR) .................. 10-2016-0140137

(51) Int. Cl.
*G01N 1/04* (2006.01)
*C12M 1/12* (2006.01)
*C12M 1/34* (2006.01)

(52) U.S. Cl.
CPC ............... *G01N 1/04* (2013.01); *C12M 25/14* (2013.01); *C12M 41/12* (2013.01)

(58) Field of Classification Search
CPC ......... G01N 1/04; C12M 25/14; C12M 41/12; B01J 19/0046; B01J 2219/00308;
(Continued)

(56) References Cited

U.S. PATENT DOCUMENTS 5,288,514 A * 2/1994 Ellman ............... A61K 49/0004
427/2.13
5,324,483 A 6/1994 Cody
(Continued)

FOREIGN PATENT DOCUMENTS

| JP | 2002-536156 A | 10/2002 |
|---|---|---|
| KR | 20140146741 A | 12/2014 |
| KR | 10-2015-0027006 A | 3/2015 |

OTHER PUBLICATIONS

Jihoon Kang et al., "High-throughput, high-content histological analysis of three-dimensional tumor spheroids by using a pillar array histo-chip", The Korean Society of Applied Pharmacology, Oct. 8, 2015.
(Continued)

*Primary Examiner* — William H. Beisner
*Assistant Examiner* — Danielle B Henkel
(74) *Attorney, Agent, or Firm* — Muncy, Geissler, Olds & Lowe, P.C.

(57) ABSTRACT

A method for producing a sample slice includes providing a disk, providing a jig on the disk for supporting side portions of a material, providing the material inside the jig, providing a pillar assembly on the jig, the pillar assembly that includes a first base member having a plurality of through holes, a second base member detachably mounted to said first base member, and a plurality of pillars supported between said
(Continued)

first and second base members and arranged to be exposed through the plurality of holes, inserting the plurality of pillars into the material, solidifying the material, separating the jig and the pillar assembly to remove the material from the jig, and cutting a sample slice from the material with a cutter.

3 Claims, 9 Drawing Sheets

(58) Field of Classification Search
CPC ...... B01J 2219/0031; B01J 2219/00373; B01J 2219/00416; B01J 2219/00423; B01J 2219/00454; B01J 2219/00493; B01J 2219/00495; B01J 2219/005; B01J 2219/00585; B01J 2219/0059; B01J 2219/00596; B01J 2219/00689; B01J 2219/00695; B01J 2219/0072; B01J 2219/00722; B01J 2219/00725; B01J 2219/00283; C07K 1/045; C07K 1/047; C40B 60/14; C40B 40/06; C40B 40/10; C40B 50/14; G06Q 10/087; G06Q 30/06
See application file for complete search history.

(56) References Cited

U.S. PATENT DOCUMENTS

| 6,932,943 | B1 | 8/2005 | Cracauer |
| 2002/0125197 | A1 | 9/2002 | Hager et al. |
| 2003/0054342 | A1 | 3/2003 | Star |
| 2012/0308449 | A1 | 12/2012 | Yang |

OTHER PUBLICATIONS

Jihoon Kang et al., "A pillar array histo-chip for high-content histological analysis of 3D tumor spheroids", FAST Functional Analysis & Screening Technologies Congress, Nov. 9, 2015.

* cited by examiner

METHOD FOR PRODUCING SAMPLE SLICE

RELATED APPLICATIONS

This application is a divisional application of U.S. Ser. No. 15/347,767, filed on Nov. 9, 2016, which claims priority to and the benefit of Korean Patent Application No. 10-2016-0029321, filed on Mar. 11, 2016 and Korean Patent Application No. 10-2016-0140137, filed on Oct. 26, 2016, the disclosure of which are incorporated herein by reference in their entirety.

TECHNICAL FIELD

The present invention relates to a method for producing a sample slice.

BACKGROUND ART

The success of new drug development depends on whether it is possible to initially derive an effective lead compound. ADME having meanings of absorption, distribution, metabolism, and excretion of the drug is a pharmacokinetic property to determine the efficacy of the drug, hence, if such a property is poor, the new drug development is to fail. Therefore, the failure rate of the new drug development has been reduced by developing in vitro evaluation models and techniques for predicting this ADME properties and applying them to early new drug screening.

Despite these efforts, in the new drug development of anticancer drugs, the situation is of still high failure rate in the clinical development stage. This may be due to lack of useful methods for anticancer efficacy evaluation. Similarly to the case of the above ADME, it needs to verify the efficacy of the anticancer drugs in the initial stage of development. The conventional efficacy assessment was based on the in-vitro 2D cell culture model, but this method could not reflect the dynamic tissue pathology of solid cancers to have a limitation to prediction of clinical efficacy. Thus, the method using 3D cell culture system that reproduces micro-environmental characteristics of tumor, such as 3-dimensinality, which is the inherent characteristic of solid cancer, and heterotypic cell interactions the anticancer agent efficacy has attracted attention as the best method for evaluating efficacy of anticancer drugs.

Bio-mimetic tissue culture system using 3-dimensional culture system is considered as a good model to study distribution and intracellular accumulation of the drug, and has also been reported for use in pharmcodynamic-pharmacokinetic evaluation. Such a three-dimensional culture system has been utilized depending on various histopathological study purposes since 1980, and recently, the 3-dimensional culture system, such as multi-layer cell culture system and multicellular spheroids, has more actively studied by a number of researchers. As an example, it has been utilized in tissue distribution study of the drug according to the cell density, evaluation of the drug showing toxicity in low oxygen and a combination experiment of anticancer drugs and radiotherapy, and the like.

Furthermore, although cancer is largely divided into blood cancers and solid cancers, the solid cancer is cancer onset in an organ such as stomach, colon and liver, which accounts for 95% or more of all the cancers. Today, large multinational pharmaceutical companies are developing new anticancer drugs, but it is a situation that the cure rate is not still improved satisfactorily for solid cancers (especially pancreatic cancer, liver cancer, kidney cancer, etc.). In particular, it is known that solid cancers, which coexist with matrix cells or extracellular matrix within the tumor microenvironment, acquire drug resistance through progress of disease via mutual contact or non-contact interaction with them. In addition, solid cancer tissues have a characteristic that is not easily accessed by drugs, and the incomplete vascular system in cancer tissues causes the imperfect blood flow and increase of the interstitial fluid pressure in tissues to rather inhibit distribution of drugs in tissues, and consequently, serves as a factor degrading the anti-cancer effect. Similarly, the extracellular matrix (ECM) also affects the permeability of the drug to have an adverse effect on the anti-cancer effect. In light of this, in order to increase the development success rate of new anticancer agents, a system is required, which can assess efficacy and tissue permeability in the early stages of development and predict efficacy and tissue distribution in vivo or clinically together.

Under such a background, three-dimensional cell culture techniques for evaluation in the bio-mimetic model have been developed, and techniques to analyze cytotoxicity in such a three-dimensionally cultured cells and the expression changes in the intracellularly or extracellularly expressed biopolymeric materials (proteins, nucleic acids, glycoproteins), etc., have been urgently needed. Currently, techniques based on tracers or dyes to track the changes and fluorescent microscopes have been developed and used, but it is a situation to obtain incomplete results only due to the optical limit and the limit to permeability of these materials themselves. Therefore, although there is a demand for techniques manufacturing tissue slices to improve such a conventional problem, the techniques that may be easily used by the experimenter are still incomplete, because the three-dimensionally cultured cells may not be easily handled through various processes with maintaining their structure and state completely (Korea Laid-open Patent Publication No. 2015-0027006).

SUMMARY OF THE INVENTION

The technical problem of the present invention is to provide a pillar assembly, which can change the arrangement of pillars, and an apparatus for producing a sample block comprising the same.

In addition, the technical problem of the present invention is to provide a pillar assembly, which can easily obtain sample slices from the sample block, and an apparatus for producing a sample block comprising the same.

In order to solve the above problems, according to one aspect of the present invention, a method for producing a sample slice comprises providing a disk, providing a jig on the disk for supporting side portions of a material, providing the material inside the jig, providing a pillar assembly on the jig, the pillar assembly that includes a first base member having a plurality of through holes, a second base member detachably mounted to said first base member, and a plurality of pillars supported between said first and second base members and arranged to be exposed through the plurality of holes, inserting the plurality of pillars into the material, solidifying the material, separating the jig and the pillar assembly to remove the material from the jig, and cutting a sample slice from the material with a cutter.

As described above, the pillar assembly and the apparatus for producing a sample block comprising the same, related to at least one example, have the following effects.

In the pillar assembly, a plurality of base members supporting the pillars is detachably combined through the fixing member such as a magnet, so that the arrangement of the pillars may be changed. Thus, in accordance with each process of preparing a sample block the arrangement of the pillars can be easily changed.

Also, it is possible to easily align and assemble the jig and the pillar assembly for producing the sample block through the solidified material. Furthermore, if solidification (e.g., freezing) of the solidified material is completed, the jig and the pillar assembly can be separated from the sample block. Moreover, the sample slices may be obtained by cutting the sample block in a state of the separated jig and pillar assembly.

In addition, the pillar assembly is separated to form holes having a predetermined depth on the sample block, and a sample is attached to the floor surfaces of the holes. At this time, the slicing of the sample is carried out from the floor surfaces of the holes, so that the sample slices can be easily and accurately obtained.

DETAILED DESCRIPTION

Hereinafter, the pillar assembly and the apparatus for producing a sample block comprising the same according to one example of the present invention are explained in detail with reference to the attached drawings.

In addition, regardless of the reference numerals, the same or similar reference numerals are given to the same or corresponding components, for which redundant description will be omitted, and the size and shape of each illustrated structural member can be exaggerated or reduced for convenience of description.

Figure 1:
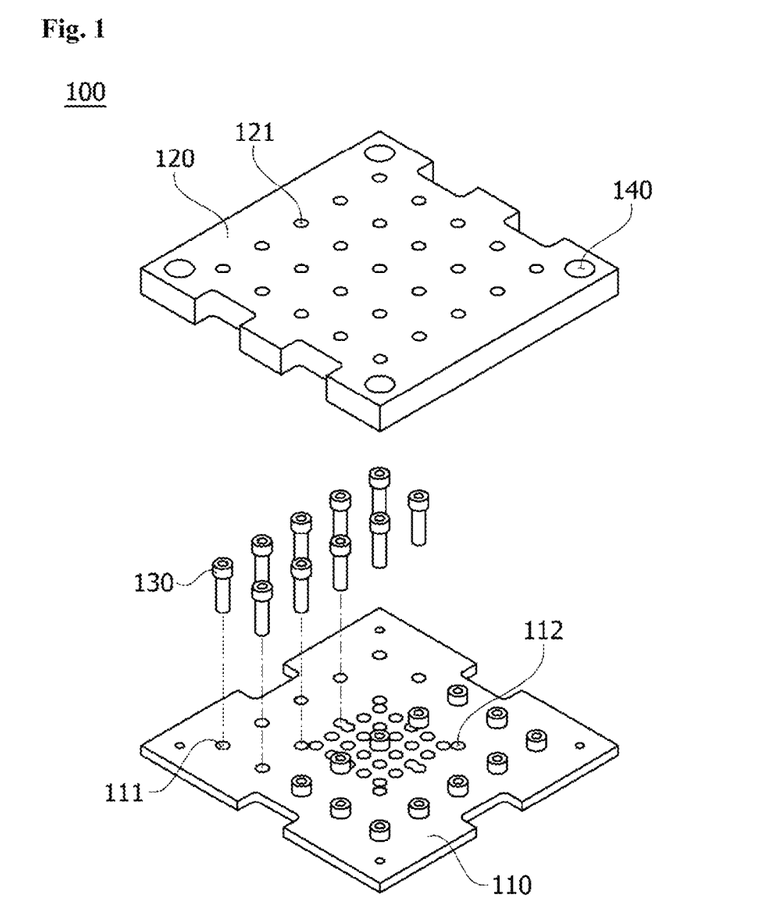
FIG. 1 is an exploded perspective view showing the pillar assembly related to one example of the present invention.
Figure 2:
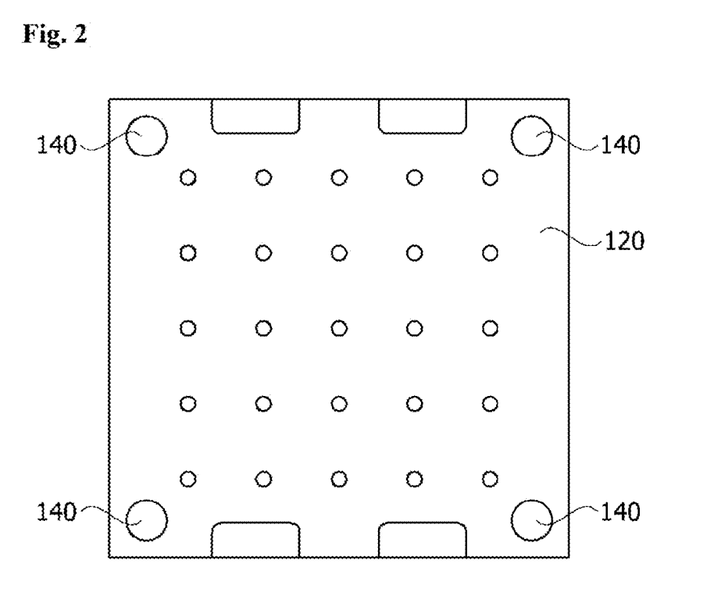
FIG. 2 is a plan view in the assembled state of the pillar assembly illustrated in FIG. 1.
Figure 3:
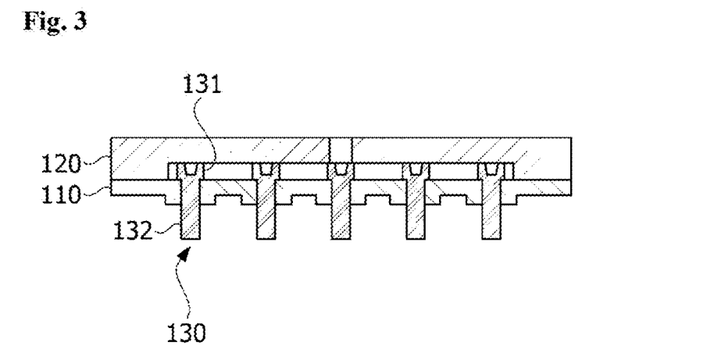
FIG. 3 is a cross-sectional view in the assembled state of the pillar assembly illustrated in FIG. 1.

FIG. 1 is an exploded perspective view showing the pillar assembly (100) related to one example of the present invention, FIG. 2 is a plan view in the assembled state of the pillar assembly (100) illustrated in FIG. 1, and FIG. 3 is a cross-sectional view in the assembled state of the pillar assembly (100) illustrated in FIG. 1.

The pillar assembly (100) related to one example of the present invention may be a pillar assembly (100) used in an apparatus for producing a sample block. In addition, the pillar assembly (100) includes a first base member (110) and a second base member (120) and a plurality of pillars (130) and a fixing member (140). Specifically, the pillar assembly (100) includes a first base member (110) having a plurality of through holes (111, 112), and a second base member (120) mounted to the first base member (110), a plurality of pillars (130) supported between the first and second base members (110, 120) and arranged to be exposed to the outside through each through hole (111, 112) and a fixing member (140) provided so as to detachably fix the first and second base members (110, 120).

Also, the first base member (110) and the second base member (120) may be a plate having a predetermined thickness. Furthermore, the first base member (110) and the second base member (120) may be formed of a metallic material. When the first base member (110) and the second base member (120) are combined, a space portion may be provided between them for part of the pillar area (e.g., head portion) to be placed and supported. The space portion may be also provided to have the same thickness as one of the head portion (131) of the pillar (130).

Besides, the pillar (130) may include a head portion (131) and a rod portion (132) extending from the head portion (131). The head portion (131) may be provided to have a diameter larger than one of the rod portion (132). The head portion (131) of the pillar (130) is placed in a space between the first base member (110) and the second base member (120) in a state that the first base member (110) and the second base member (120) combine. Furthermore, the rod portion (132) of the pillar (130) passes through the through holes (111, 112) of the first base member (110) to be exposed to the outside. Moreover, the bio-matrix, which will be described later, and cells are attached to the surface of the rod portion (132) of the pillar (130).

In addition, the length and diameter, and the like of the pillar (130) may be determined in various ways depending on the size and type of the sample block. In one example, a full length of the rod portion (132) of the pillar (130) may be about 7.1 mm, and the length of the rod portion (132) exposed to the outside of the first base member (110) may be about 4.1 mm. Furthermore, the diameter of the rod portion (132) may be about 2 mm, and the total thickness of the pillar assembly (100) in the state having the placed pillar may be about 12.1 mm.

The fixing member (140) may include one or more magnets (140) for securing the first and second base members (110, 120) by magnetic force. The magnet (140) may be provided on the first or second base members (110, 120). In addition, a plurality of magnets (140) may be arranged apart at a certain interval along a circumferential direction of the first or second base member (110, 120). For example, referring to FIG. 2, a plurality of magnets (140) may be provided on only the second base member (120), and each magnet (140) attached to the first base member (110) from a metal. Through such a structure, the first and second base members (110, 120) are removable. Furthermore, when the first and second base members (110, 120) are separated, the head portion (131) of the pillar (130) disposed between them is exposed to the outside. Moreover, each base member (120) may be also formed of a polymer material, and in this case, the magnets (140) may be provided on each base member (120) to be a pair with a different polarity.

A plurality of through holes (111, 112) may comprise a plurality of first through holes (111) which is located along the edge of the first base member (110), and a plurality of second through holes (112) which is located in the central region of the first base member (110). For example, the interval between two adjacent first through holes (111) and the interval between two adjacent second through holes (112) may be differently determined from each other. In addition, a plurality of first through holes (111) may be arranged in turn along a predetermined axial direction, and a plurality of second through holes (112) may be arranged in the central area to achieve a circle. Furthermore, the first through holes (111) may be formed the same as the well arrangement of a well plate that the pillar assembly (100) is immersed. For example, referring to FIG. 1, a plurality of first through holes (111) may be provided in a 5×5 lattice arrangement over the entire area from the edge side of the first base member (110) to the central area side. Moreover, a plurality of third through holes (121) may be provided on the second base member (120). At this time, each third through hole (121) is provided to have the same size as the first through hole (111). In addition, a plurality of third through holes (121) may have the same arrangement as one of a plurality of first through holes (111). For example, a plurality of third through holes (121) may be provided in a 5×5 lattice arrangement over the entire area from the edge side of the second base member (120) to the central area side. Furthermore, in a state that the first base member (110) and the second base member (120) combine, it is preferred that each first through hole (111) and each third through hole (121) corresponding thereto are coaxially arranged.

Meanwhile, in the cases of exposing the pillars (130) through a plurality of first through holes (111) to the outside and exposing the pillars (130) through a plurality of second through holes (112) to the outside, the arrangement of pillars may be different from each other. Accordingly, the arrangement of pillars may be easily changed depending on each process of producing the sample block.

Figure 4:
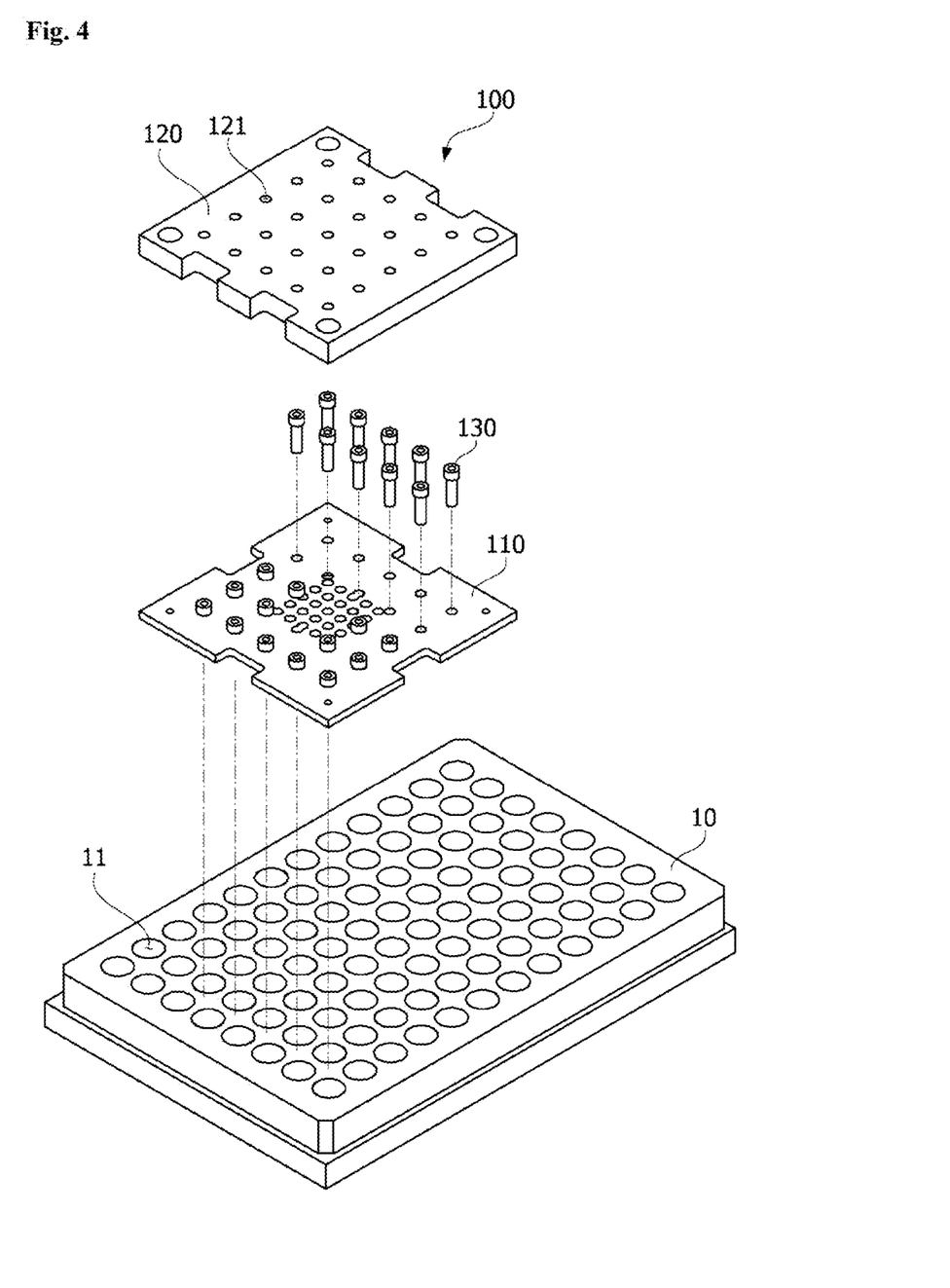
FIG. 4 is a perspective view for explaining one usage state of the pillar assembly illustrated in FIG. 1.
Figure 5:
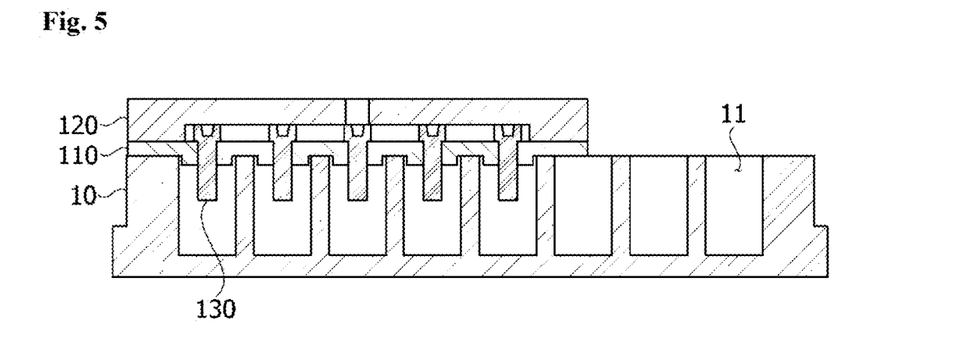
FIG. 5 is a cross-sectional view in the combined state of each component of FIG. 4.
Figure 6:
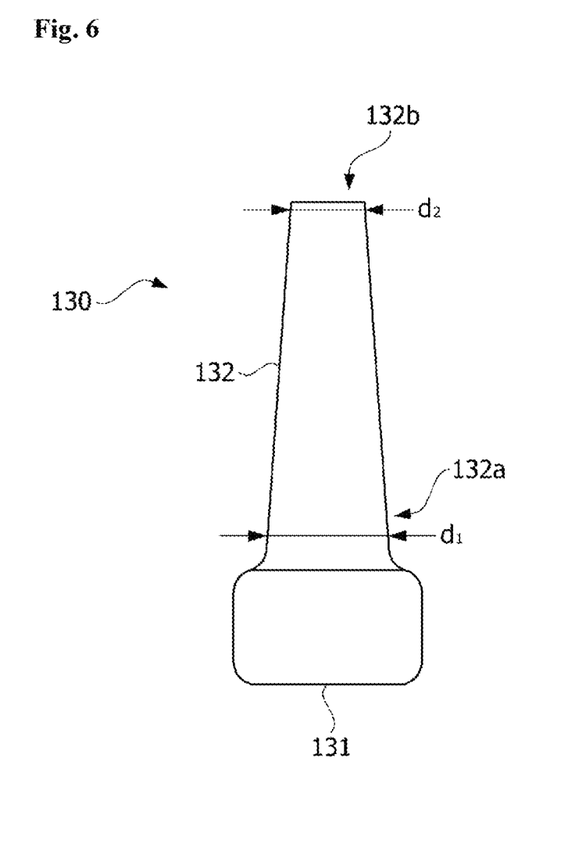
FIG. 6 is a side view showing a pillar.

FIG. 4 is a perspective view for explaining one usage state of the pillar assembly (100) illustrated in FIG. 1, FIG. 5 is a cross-sectional view in the combined state of each component of FIG. 4, and FIG. 6 is a side view showing a pillar (130).

First, in order to produce the sample block (20, see FIG. 8), the bio-matrix is attached to the surfaces of the pillars (130) and the pillars (130) of the pillar assembly (100) are immersed in the well plate (10) that a plurality of wells (well) containing a culture solution is arranged. For example, the well plate (10) may be a 96-well plate. At this time, cells may be 3-dimensionally cultured on the surfaces of the pillars (130) by immersing each pillar (130) in the wells (11). Then, in order to analyze the reactivity of drug in the cells, after reacting with a drug the cells 3-dimensionally cultured in the pillars (130), it can be transferred to the solidified material to form the sample block (20).

Meanwhile, the bio-matrix may be hereby collagen or alginate, and the cells may be cancer cells or stem cells. In addition, a candidate drug may be added to the culture solution in the well plate (10). Specifically, a "biological sample" may hereby include blood and other liquid samples of biological origin, biopsy specimens, solid tissue samples such as tissue cultures or cells derived therefrom, and more particularly, be tissues, extracts, cell lysates, whole blood, plasma, serum, saliva, ocular fluid, cerebrospinal fluid, sweat, urine, milk, ascitic fluid, synovial fluid, peritoneal fluid, and the like, and preferably cell samples, most preferably cancer cells or stem cells, but not limited thereto. The sample can be subjected to pretreatment prior to use, which may include, for example, filtration, distillation, extraction, concentration, inactivation of interfering components, addition of reagents, and the like. In addition, the "bio-matrix" is a substance that provides a space in which the cells are three-dimensionally cultured, and preferably may be bFGF (fibroblast growth factor)-alginate, heparin-alginate, polyglycolic acid, polyglycolic acid-collagen, laminin, matrigel, fibrin, collagen or alginate hydrogel, but is not limited thereto, as long as it has biocompatibility. Furthermore, the adhesive force between the surfaces of the pillars (130) and the bio-matrix can be further enhanced by treating the surfaces of the pillars (130) with any one compound selected from the group consisting of poly-L-lysine, poly-D-lysine, and dopamine and a compound containing a divalent metal ion such as $Mg^{2+}$, $Ca^{2+}$, $Ba^{2+}$, and $Cu^{2+}$.

In addition, the pillar (130) may have smaller diameter as it is more distant from the through hole (111). As described above, the pillar (130) includes a head portion (131) and a rod portion (132), wherein the rod portion (132) may be provided to have smaller diameter as at least part of an area is more distant from the through hole (111). That is, the diameter of the head portion (131) and the adjacent region (132a) (d1, for example, 2.22 mm) is formed higher than the diameter of the head portion (131) and the distant region (132b) (d2, for example, 1.98 mm). For example, the rod portion (132) may have a conical shape.

Figure 7:
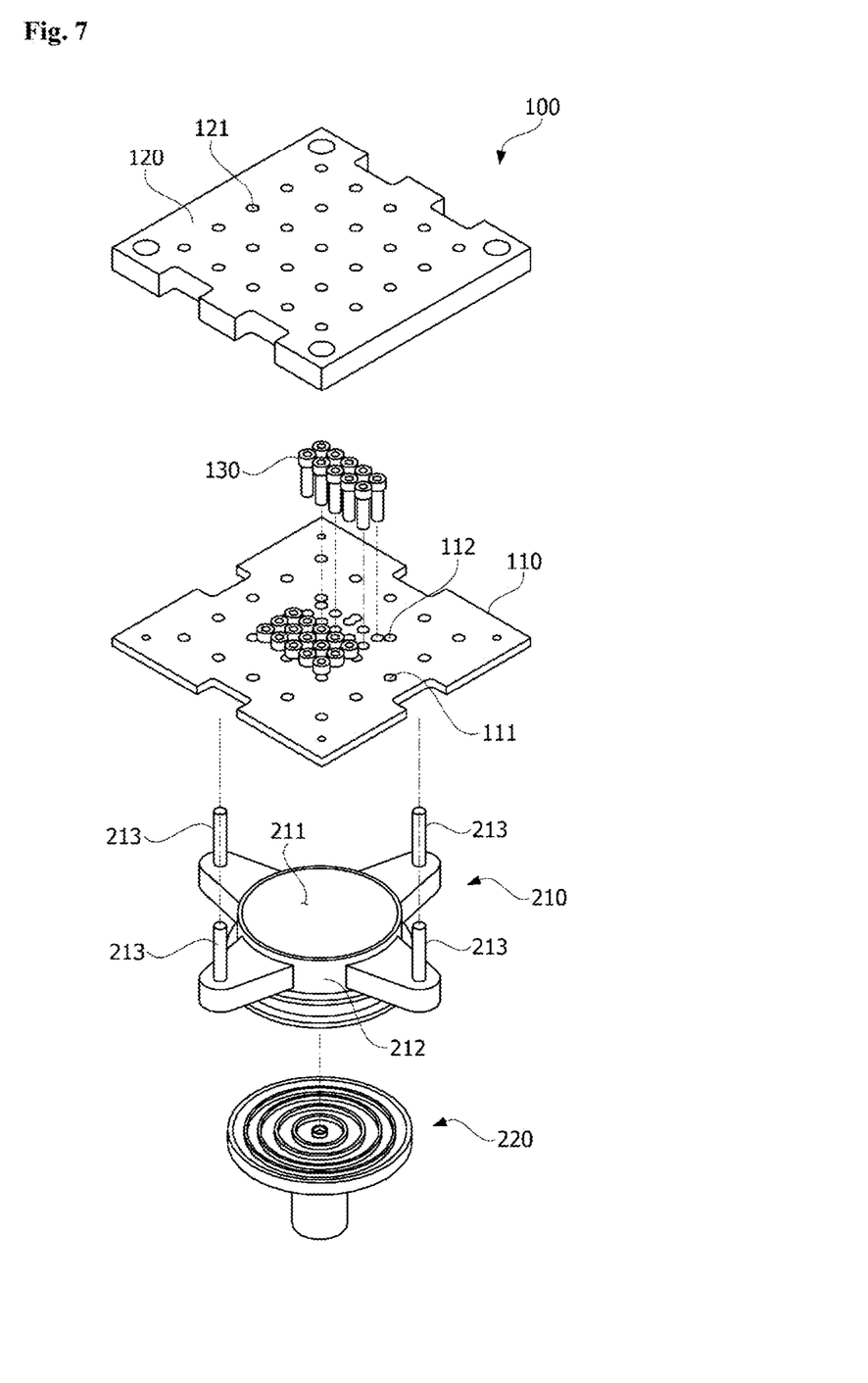
FIG. 7 is an exploded perspective view showing an apparatus for producing a sample block related to one example of the present invention.
Figure 8:
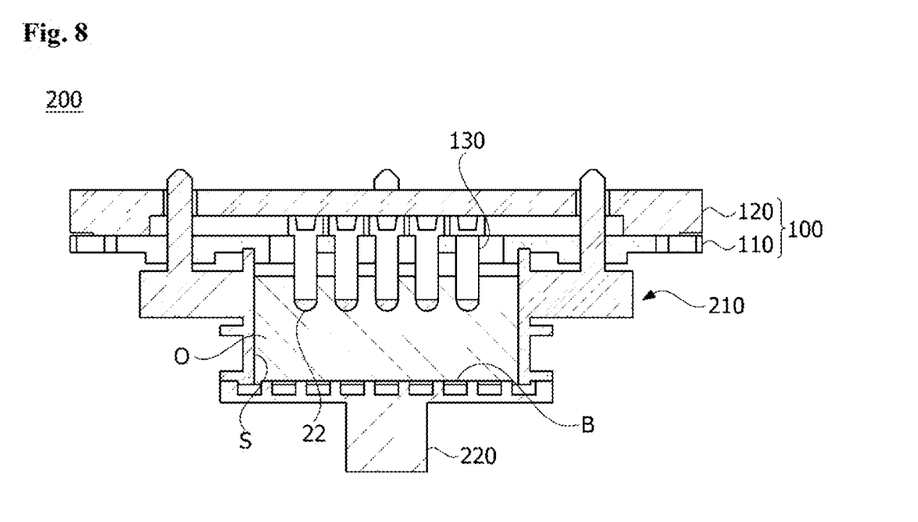
FIG. 8 is a cross-sectional view in the combined state of each component of FIG. 7.
Figure 9:
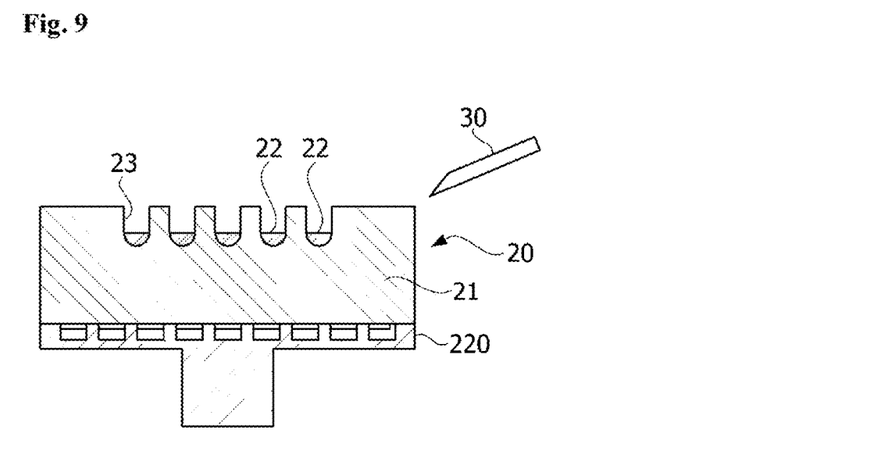
FIGS. 9 and 10 are cross-sectional views for explaining one usage state of the apparatus for producing a sample block illustrated in FIG. 7.
Figure 10:
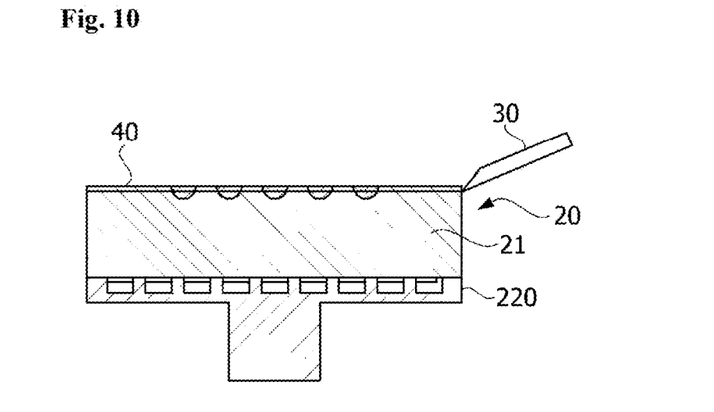

FIG. 7 is an exploded perspective view showing an apparatus for producing a sample block (200) related to one example of the present invention, FIG. 8 is a cross-sectional view in the combined state of each component of FIG. 7, and FIGS. 9 and 10 are cross-sectional views for explaining one usage state of the apparatus for producing a sample block illustrated in FIG. 7.

Referring to FIGS. 7 and 8, the apparatus for producing a sample block (200) comprises a disk (220) for supporting the bottom portion (B) of the solidified material (O), and a jig (210), which is seated on the disk (220), for supporting the side portions (S) of the solidified material (O) and a pillar assembly (100) that at least part of an area having the bio-matrix attached toward the top of the solidified material (O) is inserted inside the jig (210).

The pillar assembly (100) is the same as the pillar assembly (100) described through FIG. 1, and specifically, the pillar assembly (100) comprises a first base member (110) having a plurality of through holes (111, 112), which is placed so as to face the jig (210), and a second base member (120) mounted to the first base member (110), and a plurality of pillars (130), for attaching the bio-matrix, which is supported between the first and second base members (110, 120) and arranged to be exposed to the outside through each through hole (111, 112) and a fixing member (140) provided so as to detachably fix the first and second base members (110, 120).

In the apparatus for producing a sample block (200), the pillar assembly (100) is disposed for the rod portion (132) of the pillar (130) exposed to the outside of the first base member (110) to be inserted insider the jig (210). As described above, cells treated with a drug and 3-dimensionally cultured are attached via the bio-matrix to the rod portion (132).

In the sample block (20) for making the section block, cells (22) treated with a drug and 3-dimensionally cultured are inserted into the solidified material (cell fixing substance) (O) hold inside the jig (210) via the pillars (130). Then, if they are subjected to freezing in a state that the pillars (130) are inserted to complete the solidification, the sample block (20) is formed. Here, the solidified material (O) may be paraffin or a frozen tissue embedding agent (OCT compound).

As described above, a plurality of through holes (111, 112) may comprise a plurality of first through holes (111) which is located along the edge of the first base member (110), and a plurality of second through holes (112) which is located in the central area of the first base member (110). For example, the interval between two adjacent first through holes (111) and the interval between two adjacent second through holes (112) can be determined differently from each other. In addition, a plurality of first through holes (111) may be arranged in turn along a predetermined axial direction, and a plurality of second through holes (112) may be arranged in the central area to achieve a circle.

In the process (well plate immersion process) of attaching the bio-matrix to the pillars (130) and culturing the cells in three dimensions, that is, in the process of immersing the pillars having the attached bio-matrix in the culture solution, the pillars may be arranged in the first through holes (111). Unlike this, in the process of inserting them in the jig (210), the pillars (130) may be arranged in the second through holes (112). This is because the well arrangement in the well plate is different from the shape of the jig (210). Specifically, the shape of the jig (210) is subject to correspond to the shape of the disk (220). Therefore, it is also necessary to change the arrangement of the pillars (130), when the shape of the disc (220) is different from the shape that the wells are arranged in the well plate (10).

Meanwhile, the jig (210) may comprise the main body (212) to provide a space portion (211) for holding the solidified material (O) and at least one alignment rod (213) which is extended from the main body (212) and inserted into the pillar assembly (100) in order to align the pillar assembly (100) in a predetermined position on the jig (210). The main body (212) may have a cylindrical shape of the cylinder. Furthermore, the main body (212) may have a structure that the space portion (211) is opened to each of both sides. For example, referring to FIG. 8, when the space portion (211) is opened to each of vertical directions, the bottom portion of the space portion (211) may be closed by the disk (220), and the top portion of the space portion (211) may be closed by the pillar assembly (100). In addition, the alignment rod 213 may be numerously provided apart at a certain interval along a circumferential direction of the main body (212), and a plurality of alignment rods (213) each may be provided in a radial fashion along a circumferential direction of the main body (212). For example, the alignment rod (213) may be adapted to be inserted into the first through hole (111) of the first base member (110).

Meanwhile, referring to FIGS. 8 to 10, the pillar assembly (100) and the jig (210) may be detachably provided from the solidified material (20) to be solidified. The sample block (20) in a state that the pillar assembly (100) and the jig (210) each are separated comprises a solid layer (21) and a three-dimensional cell array (22) located within the solid layer (21). The 3-dimensional cell array (22) is formed by fixing the cells on the surfaces of the pillars (130) in the solid layer (21). Then, the sample slices (40) may be obtained by cutting the sample block (20) in a state that the jig (210) and the pillar assembly (100) are separated through a cutter (30). At this time, the pillar assembly (100) is separated to form holes (23) having a predetermined depth and the cutting of the sample block (20) is carried out from the floor surfaces of the holes (23), so that the sample slices (40) can be easily and accurately obtained.

Figure 11:
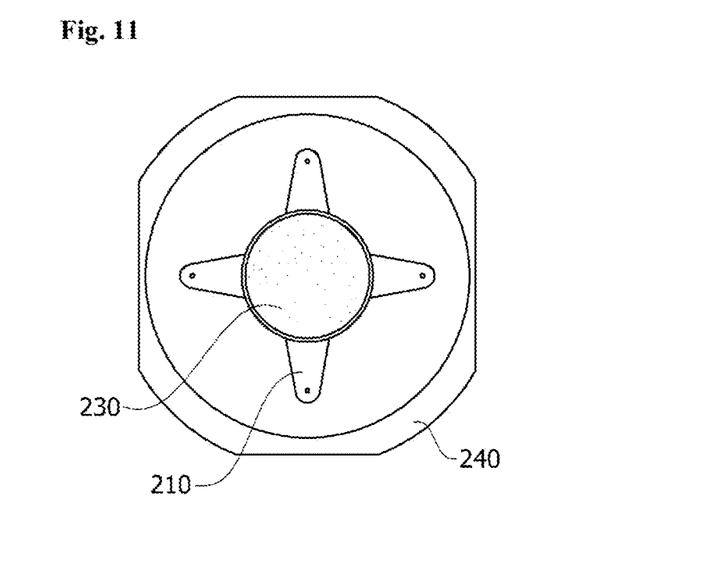
FIG. 11 is a plan view of an apparatus for producing a sample block related to another example of the present invention.
Figure 12:
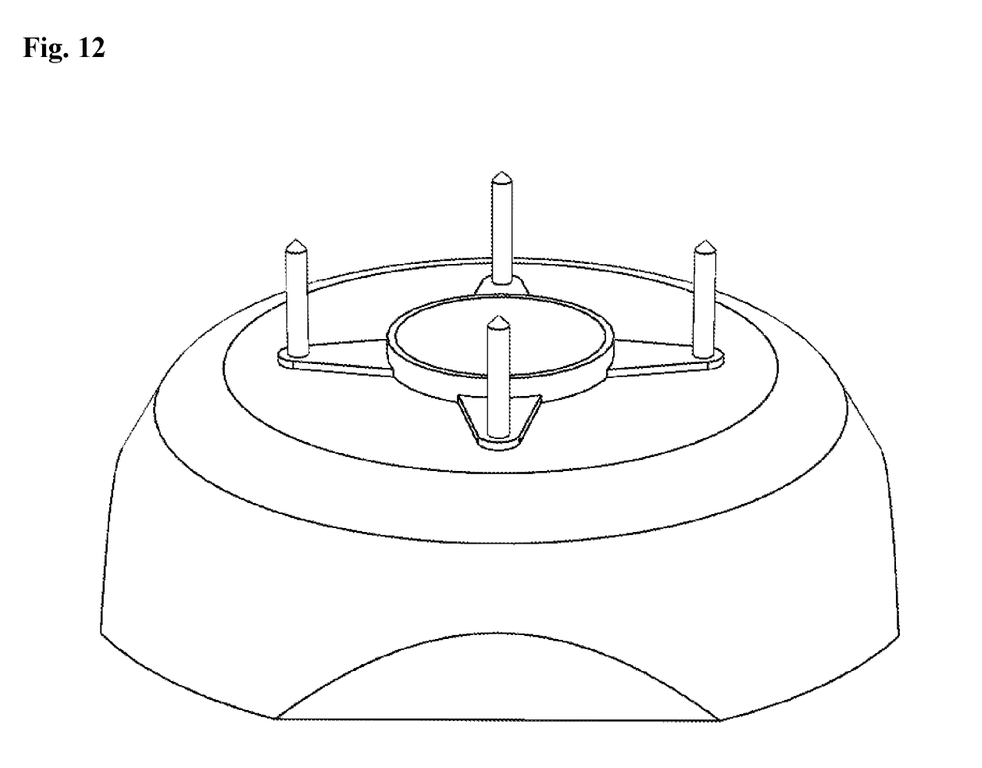
FIG. 12 is a photograph showing the apparatus for producing a sample block illustrated in FIG. 11.

FIG. 11 is a plan view showing an apparatus for producing a sample block related to another example of the present invention, and FIG. 12 is a photograph showing the apparatus for producing a sample block illustrated in FIG. 11.

Referring to FIGS. 11 and 12, the apparatus for producing a sample block can be used when the solidified material is in particular paraffin. Specifically, the apparatus for producing a sample block related to the present example comprises a thermally conductive pad (230) for supporting the bottom portion of the solidified material (paraffin), and a disk (240) on which the thermally conductive pad (230) is seated, and a jig, which is seated on the disk (240), for supporting the side portions of the solidified material and a pillar assembly that at least part of an area having the bio-matrix attached toward the top of the solidified material is inserted inside the jig.

At this time, the disk (240) may be formed of a PDMS (polydimethylsiloxane) material, and the thermally conductive pad (230) may be formed of a metallic material. That is, the shape and the material of the disk can vary depending on the kinds of the solidified material, and the thermally conductive pad may also be used additionally.

The preferred examples of the present invention as described above have been disclosed for illustrative purposes, those in the art having ordinary knowledge about the present invention will be possible to make various modifications, alterations, and additions within the spirit and scope of the present invention, and such modifications, alterations, and additions will be regarded as belonging to the claims below.

DESCRIPTION OF REFERENCES

1. 100: Pillar assembly
2. 200: Apparatus for producing a sample block
3. 210: Jig
4. 220, 240: disc
5. 230: Thermally conductive pad

What is claimed is:
1. A method for producing a sample slice, comprising:
providing a disk;
providing a jig on the disk for supporting side portions of a material;
providing the material inside the jig;
providing a pillar assembly on the jig, the pillar assembly comprising:
a first base member having a plurality of through holes;
a second base member detachably mounted to said first base member;
a plurality of pillars, for attaching a bio-matrix, the bio-matrix being supported between said first base member and said second base member members and arranged to be exposed to an outside of the pillar assembly through each of the plurality of through holes, each of the plurality of pillars comprising:
a head portion disposed in a space between said first base member and said second base member such that the first base member is combined with the second base member; and
a rod portion extending from the head portion, the rod portion having a diameter smaller than a diameter of the head portion, and the rod portion passing through one of the plurality of through holes of the first base member to the outside of the pillar assembly; and
a fixing member provided to detachably fix said first base member to said second base member;
inserting the plurality of pillars into the material;
solidifying the material by freezing;
separating the jig and the pillar assembly from a sample block made from the material; and
obtaining sample slices by cutting the sample block, wherein the bio-matrix and cells in the bio-matrix are attached to a surface of the rod portion of the plurality of pillars.

2. The method for producing the sample slice according to claim 1, further comprising:

attaching the bio-matrix on the plurality of pillars;
immersing the plurality of pillars into a culture solution; and
culturing cells three-dimensionally on the plurality of pillars.

3. The method for producing the sample slice according to claim 1, further comprising providing a thermally conductive pad on the disk.

* * * * *